United States Patent [19]

Freeman

[11] Patent Number: 5,431,688
[45] Date of Patent: Jul. 11, 1995

[54] METHOD AND APPARATUS FOR TRANSCUTANEOUS ELECTRICAL CARDIAC PACING

[75] Inventor: Gary A. Freeman, Newton Center, Mass.

[73] Assignee: ZMD Corporation, Wilmington, Del.

[21] Appl. No.: 93,817

[22] Filed: Jul. 19, 1993

Related U.S. Application Data

[63] Continuation-in-part of Ser. No. 28,282, Mar. 9, 1993, abandoned, which is a continuation of Ser. No. 536,968, Jun. 12, 1990, Pat. No. 5,193,537.

[51] Int. Cl.⁶ .......................................... A61N 1/362
[52] U.S. Cl. ..................................................... 607/10
[58] Field of Search ............................ 607/2, 9, 10, 72

[56] References Cited

U.S. PATENT DOCUMENTS

| 2,590,876 | 4/1952 | Landauer. | |
|---|---|---|---|
| 3,077,884 | 2/1963 | Batrow et al. | |
| 3,543,761 | 12/1970 | Bradley | 607/72 |
| 3,543,761 | 12/1970 | Bradley. | |
| 3,888,261 | 6/1975 | Maurer. | |
| 4,177,817 | 12/1979 | Bevilacqua. | |
| 4,331,157 | 5/1982 | Keller, Jr. et al. | |
| 4,448,199 | 5/1984 | Schmid. | |
| 4,787,389 | 11/1988 | Tarjan. | |
| 5,111,812 | 5/1992 | Swanson et al. | 128/419 D |
| 5,205,284 | 4/1993 | Freeman. | |

FOREIGN PATENT DOCUMENTS

| 0518546 | 12/1992 | European Pat. Off. . |
|---|---|---|
| 91/19535 | 12/1991 | WIPO. |
| 93/01861 | 2/1993 | WIPO. |

OTHER PUBLICATIONS

Alferness et al., "Multiple Extenal Pacing Electrode Summation in Dogs", Journal of Am. College of Cardiology, Feb. 1991, vol. 17, No. 2 (Supplement A).

Geddes, "A Short History of the Electrical Stimulation of Excitable Tissue Including Electrotherapeutic Applications", Supp. to the Physiologist, vol. 27, No. 1 (Feb. 1984).

Geddes et al., "Electroventilation", American Journal of Emergency Medicine, vol. 3, No. 4, pp. 338–339 (Jul. 1985).

Kahn et al., "Technical Aspects of Electrical Stimulation Devices", Med. Progr. Technol., vol. 1, No. 2, pp. 58–68 (1972).

Schechter, "Background of Clinical Electrostimulation; VII. Modern era of artificial cardiac pace makers", New York State Journal of Medicine, pp. 1166–1190 (May 15, 1972).

Primary Examiner—William E. Kamm
Assistant Examiner—Scott M. Getzow
Attorney, Agent, or Firm—Fish & Richardson

[57] ABSTRACT

Method and apparatus for transcutaneously pacing the heart using two or more pairs of electrodes to reduce patient discomfort during pacing. The pacing stimuli are divided into two or more series of pulses, with at least one series of pulses being delivered by an electrode pair that differs from an electrode pair delivering another series of pulses. Typically, the electrode pairs are arranged so that current paths between electrodes in each pair of electrodes intersect at the patient's heart.

34 Claims, 11 Drawing Sheets

METHOD AND APPARATUS FOR TRANSCUTANEOUS ELECTRICAL CARDIAC PACING

CROSS-REFERENCE TO RELATED APPLICATIONS

This is a continuation-in-part of application Ser. No. 08/028,282, filed Mar. 9, 1993 now abandoned, which itself was a continuation of an application Ser. No. 07/536,968, filed Jun. 12, 1990 now U.S. Pat. No. 5,193,537.

BACKGROUND OF THE INVENTION

This invention relates to electrically pacing the heart transcutaneously.

During transcutaneous, or external, electrical pacing of a patient's heart, electrical stimuli travel from the pacing apparatus' electrodes to the heart through the patient's skin and skeletal thorax muscles to stimulate the heart. Depending on the magnitude of the stimuli and the characteristics of a particular patient's skeletal muscles, the skeletal muscles may contract in response to the passage of the electrical stimuli through them. Similarly, the passage of the electrical pacing stimuli through the patient's skin may stimulate cutaneous nerves and muscles located near to the skin. This nerve stimulation and skeletal muscle contraction may feel uncomfortable to the patient, or even become painful enough to result in the patient's intolerance of extended transcutaneous heart pacing.

It has been shown (U.S. Pat. No. 4,349,030) that the skeletal muscle contractions and cutaneous nerve stimulation associated with conventional transcutaneous heart pacing may be reduced by lengthening the duration of electrical pacing stimuli to greater than five milliseconds.

SUMMARY OF THE INVENTION

In general, the invention features the use of two or more electrode pairs to deliver electrical pacing stimuli to a heart. The pacing stimuli are divided into two or more series of pulses, with at least one series of pulses being delivered by an electrode pair that differs from an electrode pair delivering another series of pulses. The series of pulses are timed so that the combination of all of the series results in the desired pacing stimuli.

In preferred embodiments, two pairs of electrodes are arranged so that current paths between electrodes in each pair of electrodes intersect at the patient's heart. The use of multiple electrode pairs tends to reduce the current density in the patient's skin and skeletal muscles for a desired level of current density in the patient's heart, and allows stimulation of the patient's heart with reduced or no stimulation of the patient's skin or skeletal muscles. This, in turn, tends to reduce discomfort to the patient.

Other features and advantages of the invention will be apparent from the following description of the preferred embodiments and from the claims.

DESCRIPTION OF THE PREFERRED EMBODIMENTS

Figure 1:
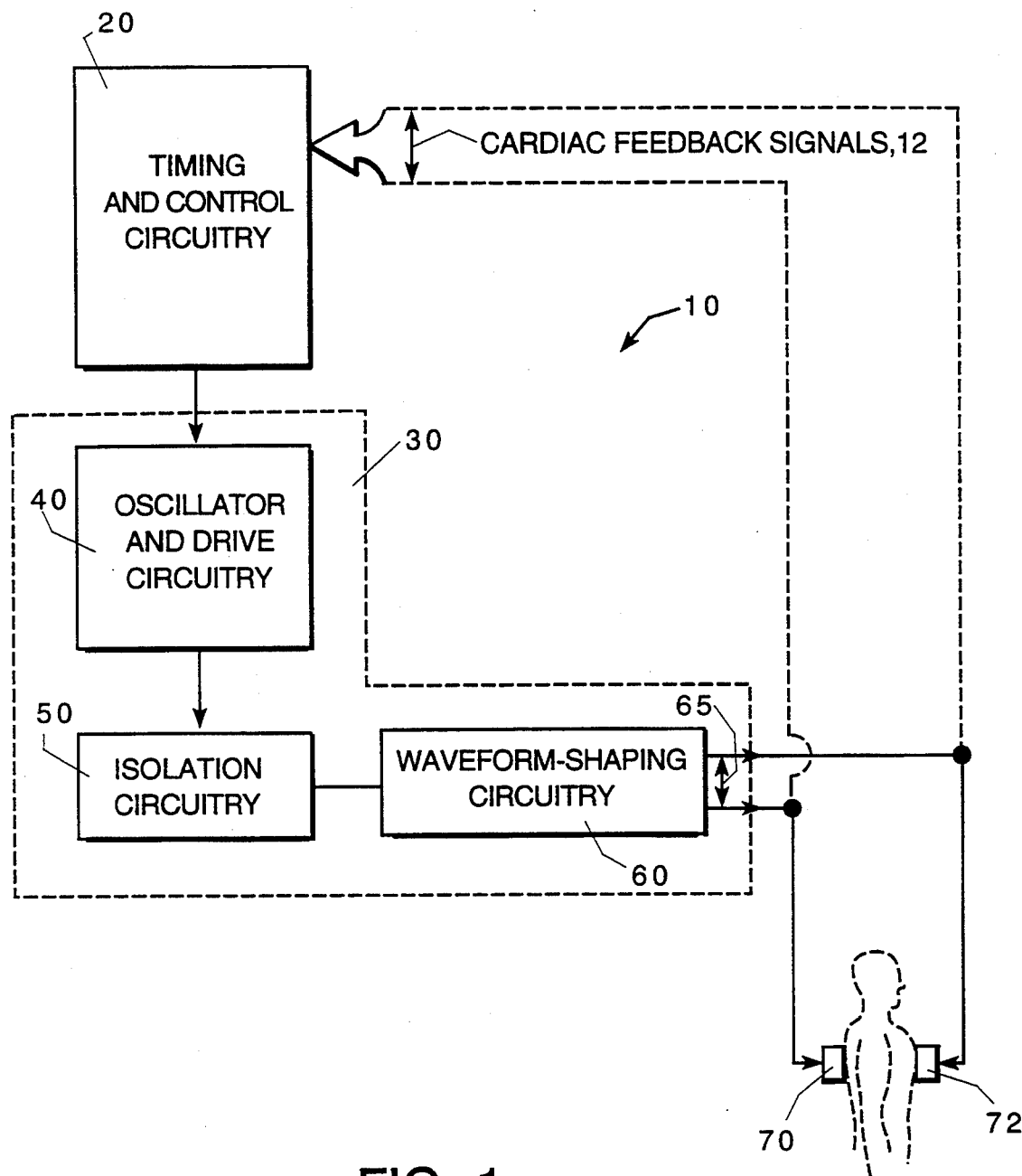
FIG. 1 is a block diagram of a pacing stimuli signal generator according to one embodiment of the invention.

Referring to FIG. 1, there is shown a signal generator 10 for generating electrical pacing stimuli 65 which are to be applied transcutaneously to a patient's heart. The signal generator's timing and control circuitry 20 can accept cardiac feedback signals 12 from the patient to initiate electrical pacing stimuli, or it can operate without such feedback (asynchronous pacing). The timing and control circuitry also sets the timing characteristics of the pacing stimuli, as discussed below. The timing and control circuitry 20 initiates the pacing stimuli by signaling the stimuli generating circuitry 30, which includes oscillator and drive circuitry 40, isolation circuitry 50, and waveform-shaping circuitry 60. Oscillator and drive circuitry 40 generates a stream of pulses that are processed by isolation circuitry 50, which isolates the signal generator's internal voltages from the patient, thereby providing electrical hazard protection for the patient during the patient's exposure to the pacing stimuli 65.

Waveform-shaping circuitry 60 receives the isolation circuitry's pulse stream output and modifies signal characteristics of the pulse stream, e.g., pulse shape, polarity, and amplitude, to generate pacing stimuli 65 having user-specified signal parameters. At the signal generator's output, the pacing stimuli 65 are coupled to posterior and anterior electrodes 70, 72, which together externally deliver the electrical stimuli to the patient for transcutaneous pacing of the patient's heart.

Figure 2:
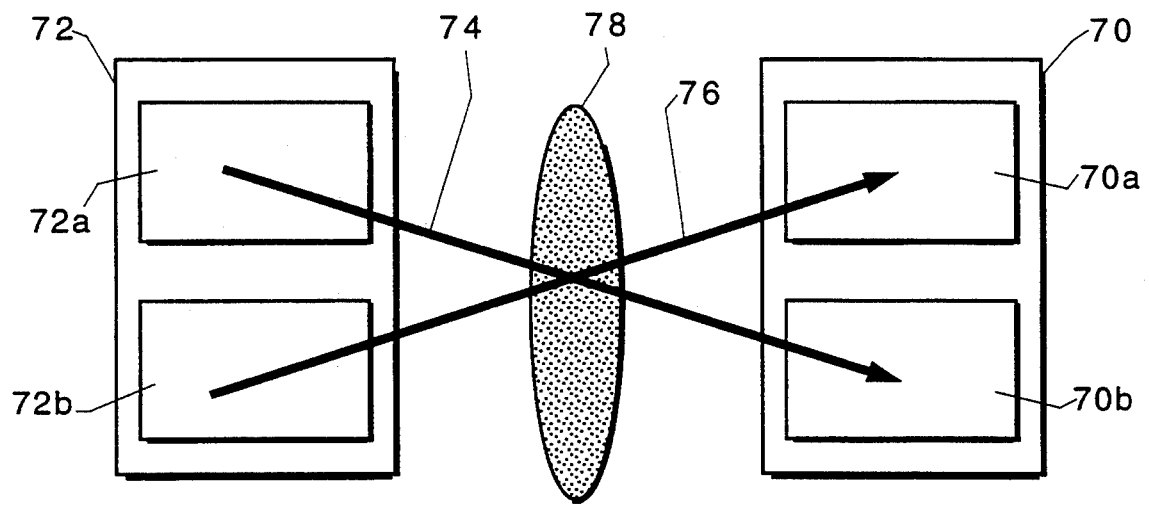
FIG. 2 is a schematic of an electrode configuration according to the invention.

Referring to FIG. 2, posterior and anterior electrodes 70, 72 are connected to the signal generator 10 so that current flows in a path 74 from a region 72a of electrode 72 to a region 70b of electrode 70 and in a path 76 from a region 72b of electrode 72 to a region 70a of electrode 70. Electrodes 70, 72 are arranged so that current paths 74, 76 intersect at the patient's heart 78.

Figure 3:
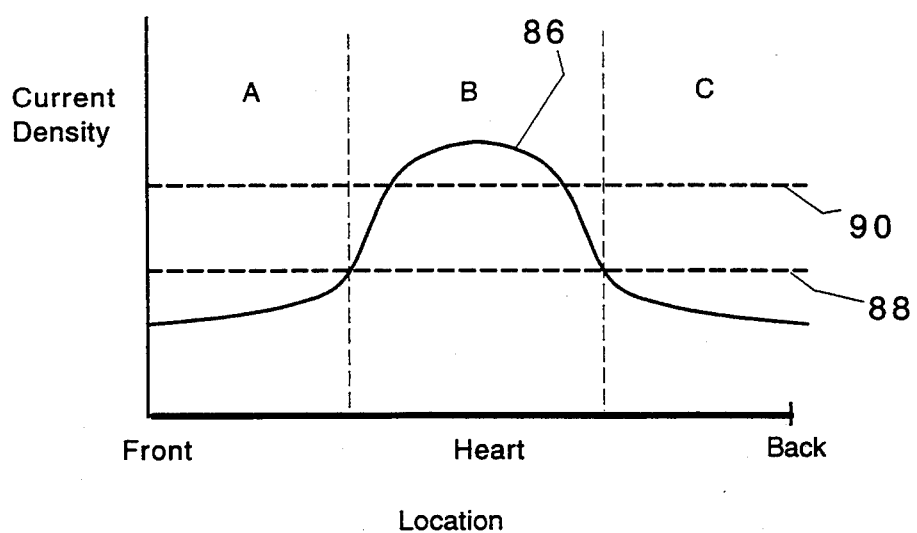
FIG. 3 is a graph of the relative current density produced by the electrode arrangement of FIG. 2.

Referring also to FIG. 3, when electrodes 70, 72 are arranged as shown in FIG. 2, current density 86 is substantially increased at the heart 78 relative to other locations in the patient's thoracic cavity. The increased current density results from the intersection of paths 74, 76 at the heart 78. As a result of the uneven distribution of current density, pacing stimuli can be produced so that current density 86 outside the heart (regions A, C) is below a level 88 necessary for stimulation of skeletal muscle, while current density 86 at the heart (region B) exceeds a level 90 necessary for stimulation of cardiac muscle. Such stimuli provide effective transcutaneous stimulation of the heart with reduced patient discomfort from skeletal muscle contraction.

Figure 4A:
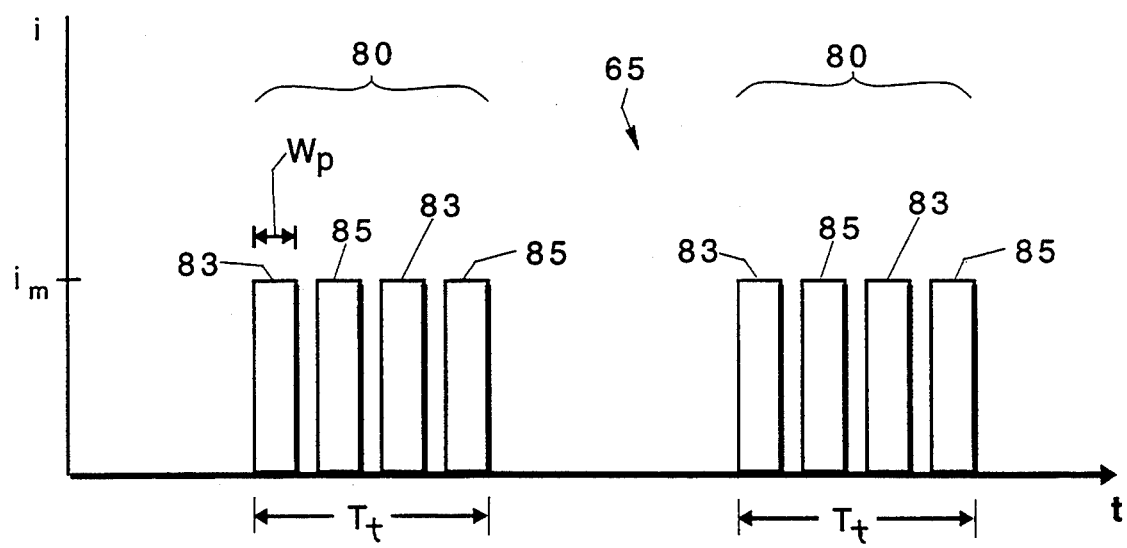
FIGS 4A, 4B, and 4C show an illustrative example of how electrical pacing stimuli are delivered according to the electrode arrangement of FIG. 2.
Figure 4B:
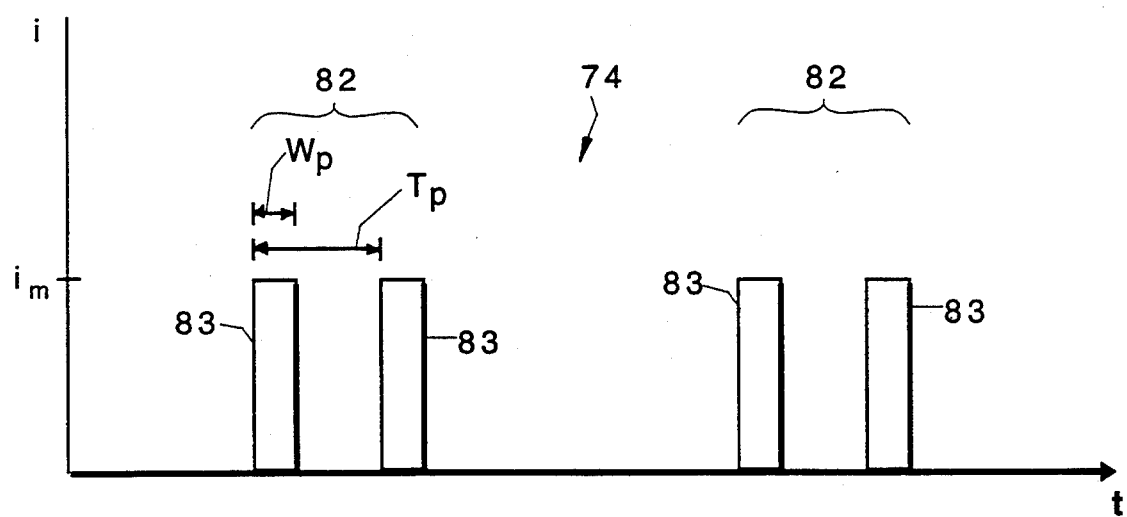
Figure 4C:
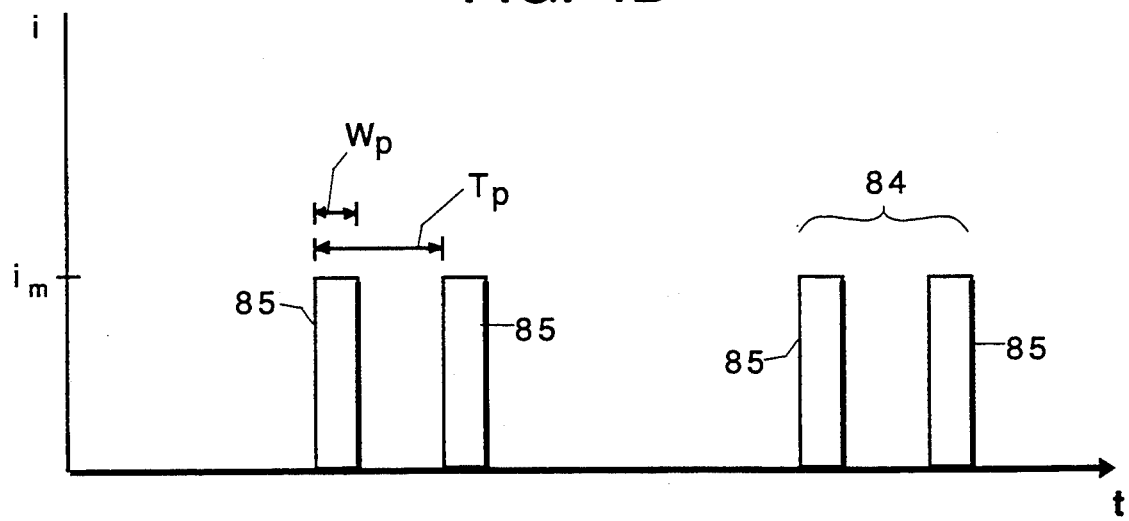

Referring also to FIGS. 4A, 4B, and 4C, the signal generator's electrical pacing stimuli output 65 (FIG. 4A) includes pacing stimuli 80 delivered to the patient to stimulate the patient's heart. In the embodiment of FIGS. 4A, 4B, and 4C, patient discomfort from skeletal muscle contraction is further reduced by dividing each pacing stimulus 80 into a pulse train including a series of pulses 83, 85, with each pulse having a time duration, or width, $W_p$, which may be different from the duration of the other pulses in the series.

Pacing stimuli 80 are time multiplexed by circuitry located either in waveform-shaping circuitry 60 or posterior and anterior electrodes 70, 72 to produce waveform 82 (FIG. 4B), which includes pulses 83 and flows along path 74, and waveform 84 (FIG. 4C), which includes pulses 85 and flows along path 76. When current flow along path 74 is desired, regions 72b and 70a are placed in a high impedance mode, which prevents current flow to or from regions 72b or 70a. Similarly, when current flow along path 76 is desired, regions 72a and 70b are placed in a high impedance mode, which prevents current flow to or from regions 72a or 70b. Thus, current flow is limited to paths 74, 76 by controlling the impedance of regions 70, 72.

Figure 5A:
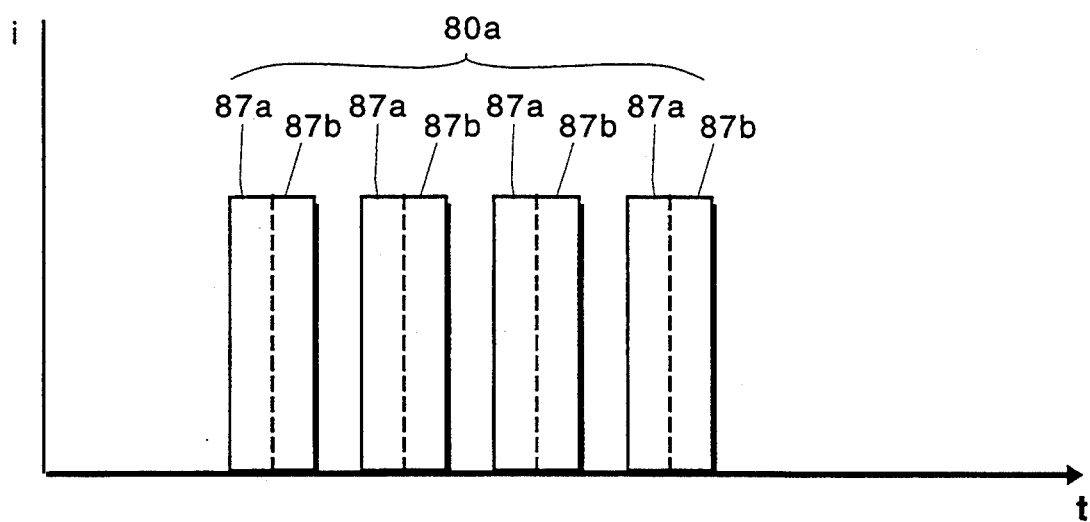
FIGS. 5A, 5B, and 5C show a second illustrative example of a way of delivering electrical pacing stimuli according to the electrode arrangement of FIG. 2.
Figure 5B:
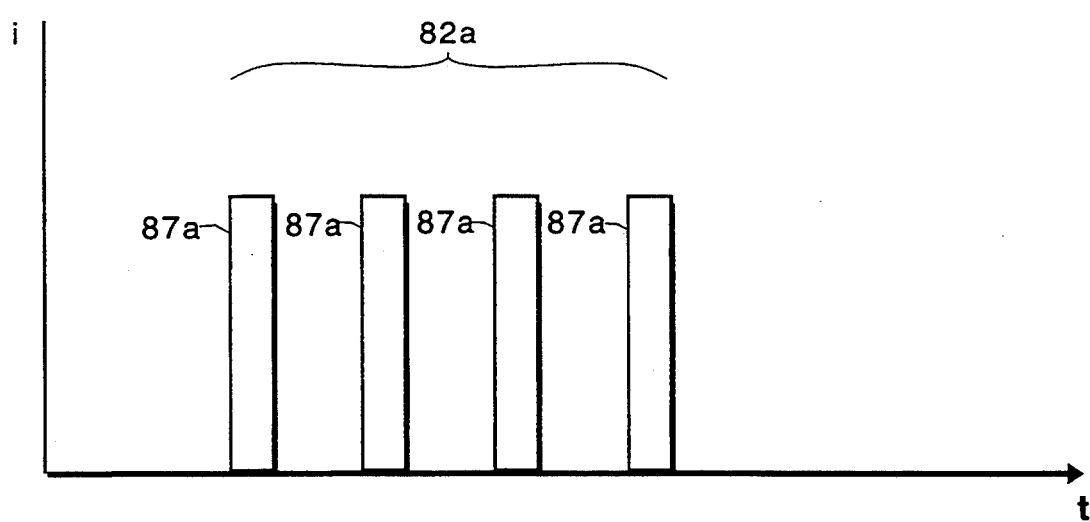
Figure 5C:
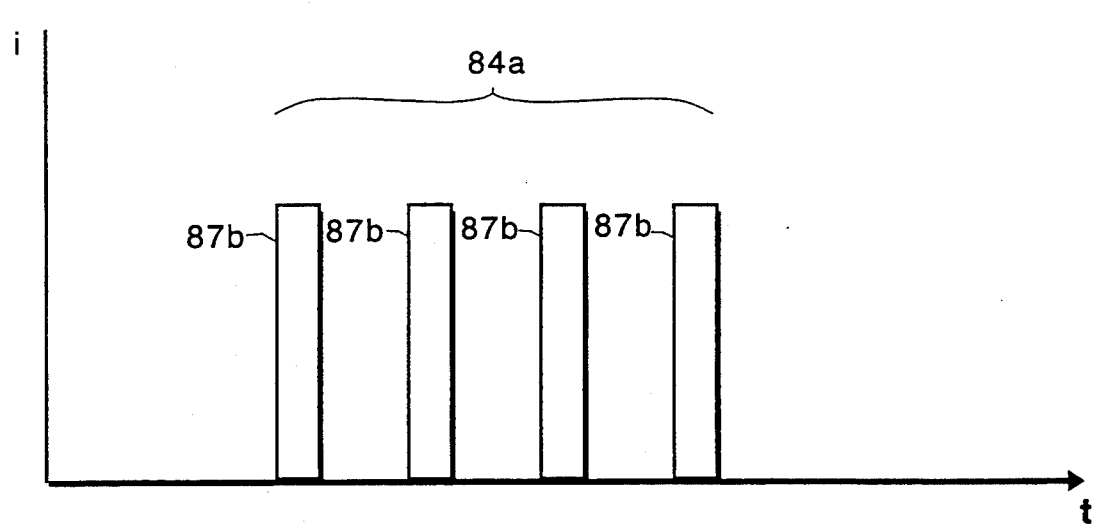

Referring to FIG. 5A, 5B and 5C, an alternative technique of time multiplexing pacing stimuli involves dividing each individual pulse between paths 74, 76. As shown in the figure, an alternative pacing stimulus 80a includes a series of pulses 87, each having a first portion 87a and a second portion 87b (FIG. 5A). Pacing stimulus 80a is time multiplexed to produce waveform 82a (FIG. 5A), which includes pulse portions 87a and flows along path 74, and waveform 84a (FIG. 5A), which includes pulse portions 87b and flows along path 76.

Figure 12A:
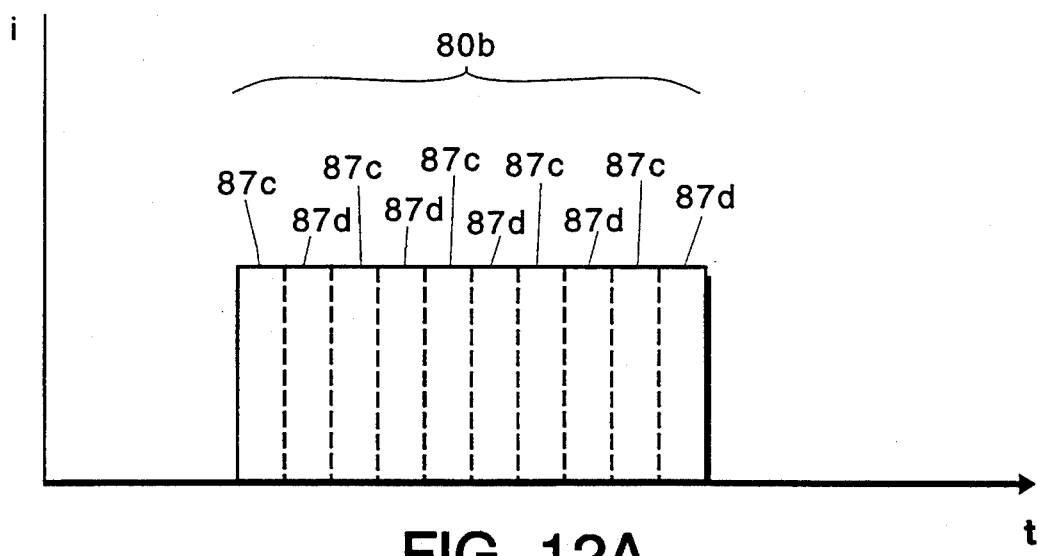
FIGS. 12A, 12B, and 12C show a third illustrative example of a way of delivering electrical pacing stimuli according to the electrode arrangement of FIG. 2.
Figure 12B:
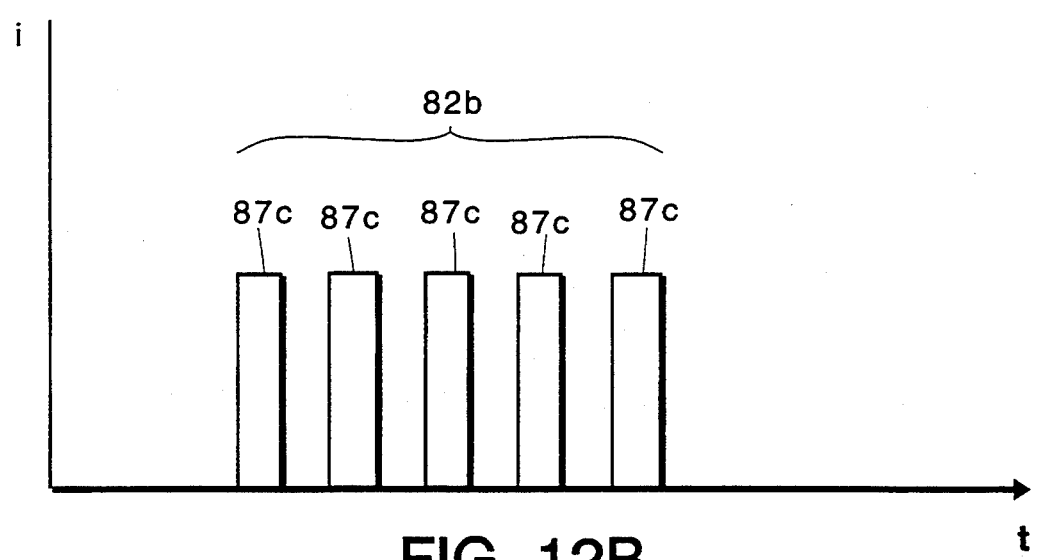
Figure 12C:
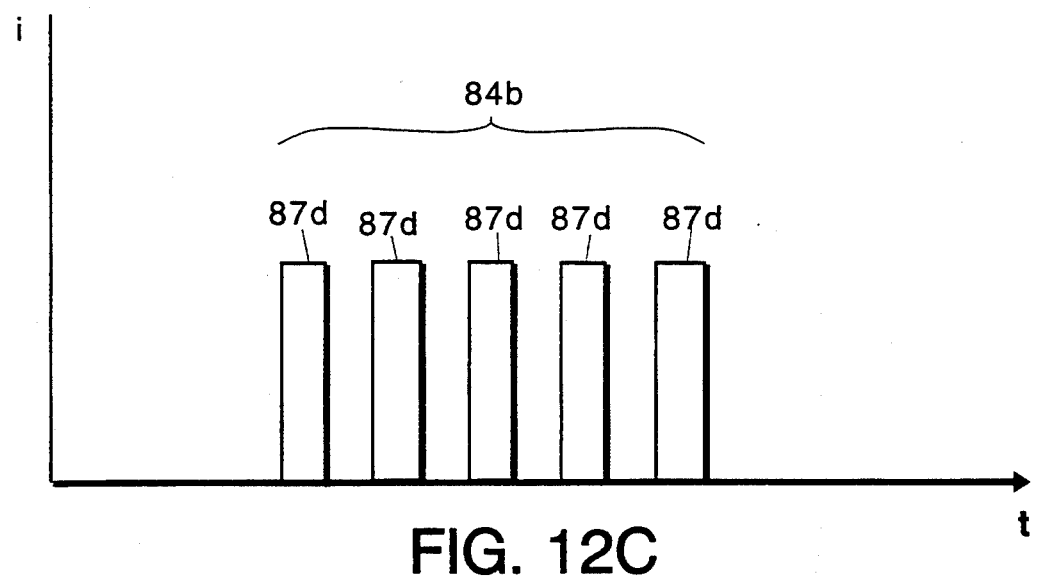

Referring to FIGS. 12A, 12B, and 12C, another alternative technique of time multiplexing pacing stimuli involves dividing a continuous pulse between paths 74, 76. As shown in the figures, an alternative pacing stimulus 80b is a continuous pulse including alternating portions 87c and 87d (FIG. 5B). Pacing stimulus 80b is time multiplexed to produce waveform 82b (FIG. 12B), which includes portions 87c and flows along path 74, and waveform 84b (FIG. 12C), which includes pulse portions 87d and flows along path 76.

Figure 13A:
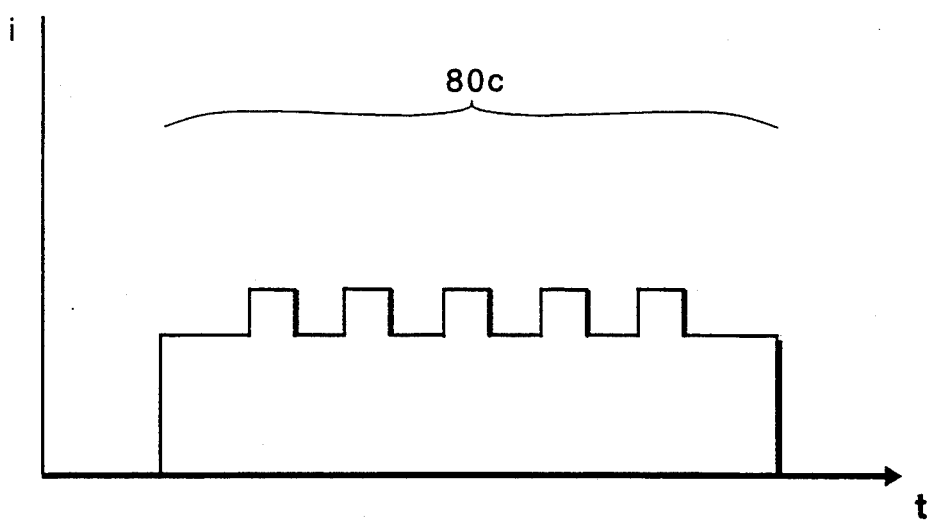
FIGS. 13A, 13B, and 13C show a fourth illustrative example of a way of delivering electrical pacing stimuli according to the electrode arrangement of FIG. 2.
Figure 13B:
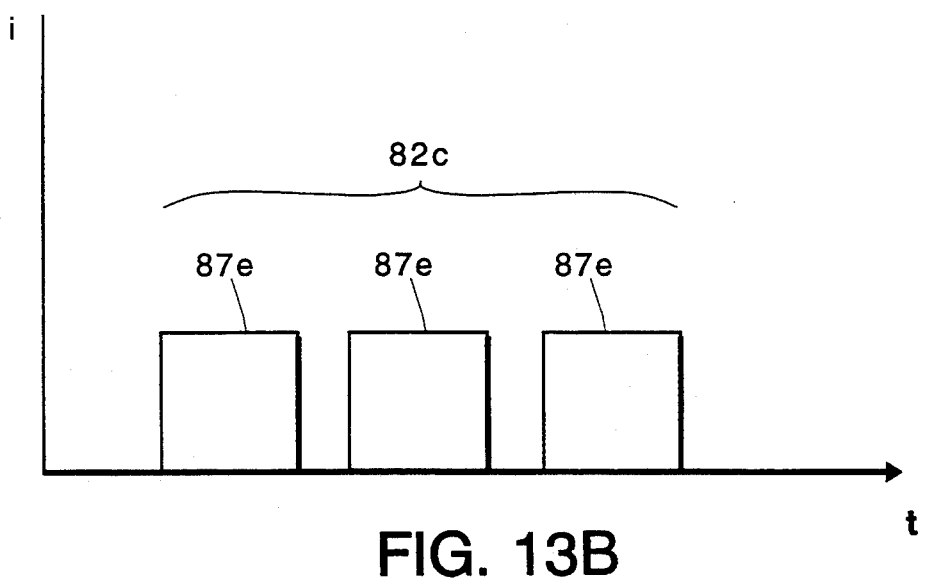
Figure 13C:
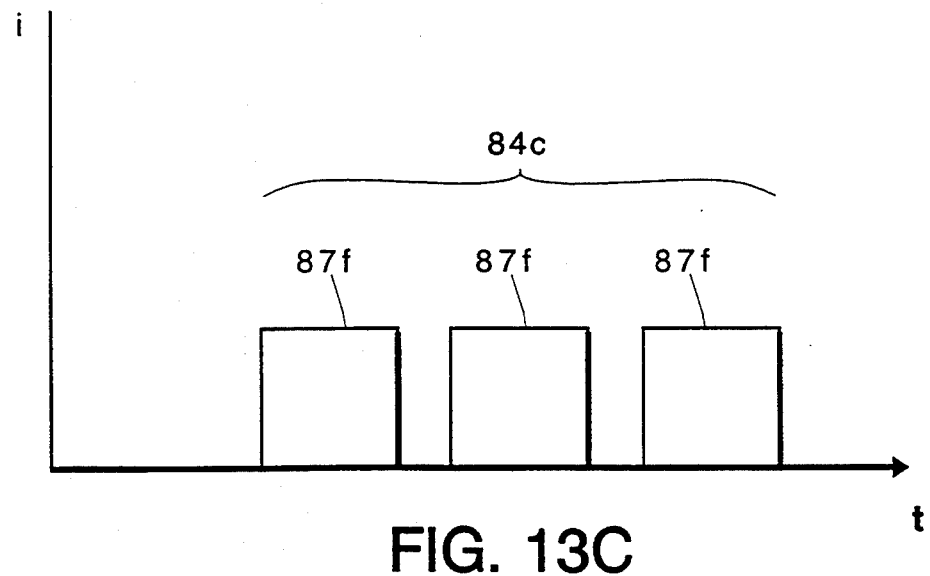

Referring to FIGS. 13A, 13B, and 13C, another alternative technique of time multiplexing pacing stimuli involves dividing a continuous pulse into overlapping waveforms flowing primarily along paths 74, 76. As shown in the figure continuous pacing stimulus 80c (FIG. 13A) is time multiplexed to produce overlapping waveforms 82c (FIG. 13C), which includes pulses 87e and flows primarily along path 74, and waveform 84c (FIG. 5C(c)), which includes pulses 87f and flows primarily along path 76. Due to the overlap of waveforms 82c and 84c, current flow is not limited to paths 74, 76 (i.e., some current flows from region 72a to region 70a and from region 72b to region 70b (see FIG. 2).

Referring to FIGS. 4A–4C and 6, there are shown characteristic curves for pulse stimuli, representing the relationship between a pulse's current amplitude, or strength, i, and a pulse's duration, t, for stimulating cardiac muscle and skeletal muscle. The duration, $T_t$, of each pacing stimuli 80 (FIGS. 4A–4C) is chosen by considering these strength-duration curves. Each curve delineates the minimum duration, t, which an electrical pulse stimulus having a given current amplitude, i, will require to stimulate a muscle. Stated another way, given a pulse amplitude, i, a muscle will not be stimulated unless the pulse duration, t, is on, or to the right of, the corresponding curve. Two different stimulus points lying on the strength-duration curve for a muscle, like points A and B on the cardiac muscle curve, will equally effectively stimulate that muscle.

A minimum pulse amplitude, or rheobase ($Ri_c$ for cardiac muscle and $Ri_s$ for skeletal muscle), defines the smallest pulse amplitude that will stimulate a muscle. Any stimulus having a current amplitude less than the rheobase will not stimulate a muscle, even if the pulse's duration is greater than the rheobase duration, called the utilization time, ($Rt_c$ for cardiac muscle and $Rt_s$ for skeletal muscle). Comparing the strength-duration curves of FIG. 6, the cardiac muscle's utilization time, $Rt_c$, which is greater than approximately 40 msec, is longer than that of skeletal muscle, having a utilization time $Rt_s$ which is considerably less than 40 msec.

Given these utilization times for cardiac and skeletal muscle, a preferable range for the duration $T_t$ of a pacing stimulus 80 is selected with the following consideration. While any stimulus point on the cardiac strength-duration curve produces effective cardiac stimulation, stimulus points having lower current amplitudes tend to produce lower skeletal muscle stimulation than stimulus points having higher current amplitudes, for a given stimulus duration. Accordingly, a pulse stimulus having the characteristics of point A (close to the cardiac utilization time $Rt_c$) stimulates skeletal muscle less than a pulse stimulus having the characteristics of point B, but will stimulate the heart equally effectively. Therefore, by choosing a pacing stimulus duration around the same duration as the cardiac utilization time, the heart can be adequately stimulated by the pulse train while producing less skeletal muscle stimulation than would be produced by a pulse train of shorter duration and correspondingly higher pulse current amplitudes. The total time duration, $T_t$, of each pacing pulse train is therefore preferably at least 5 msec, or more preferably 20 msec, but may be of any duration sufficient to stimulate the heart. The maximum preferable pacing pulse train duration is limited to approximately 150 msec because of safety considerations for inducing cardiac fibrillation.

Figure 6:
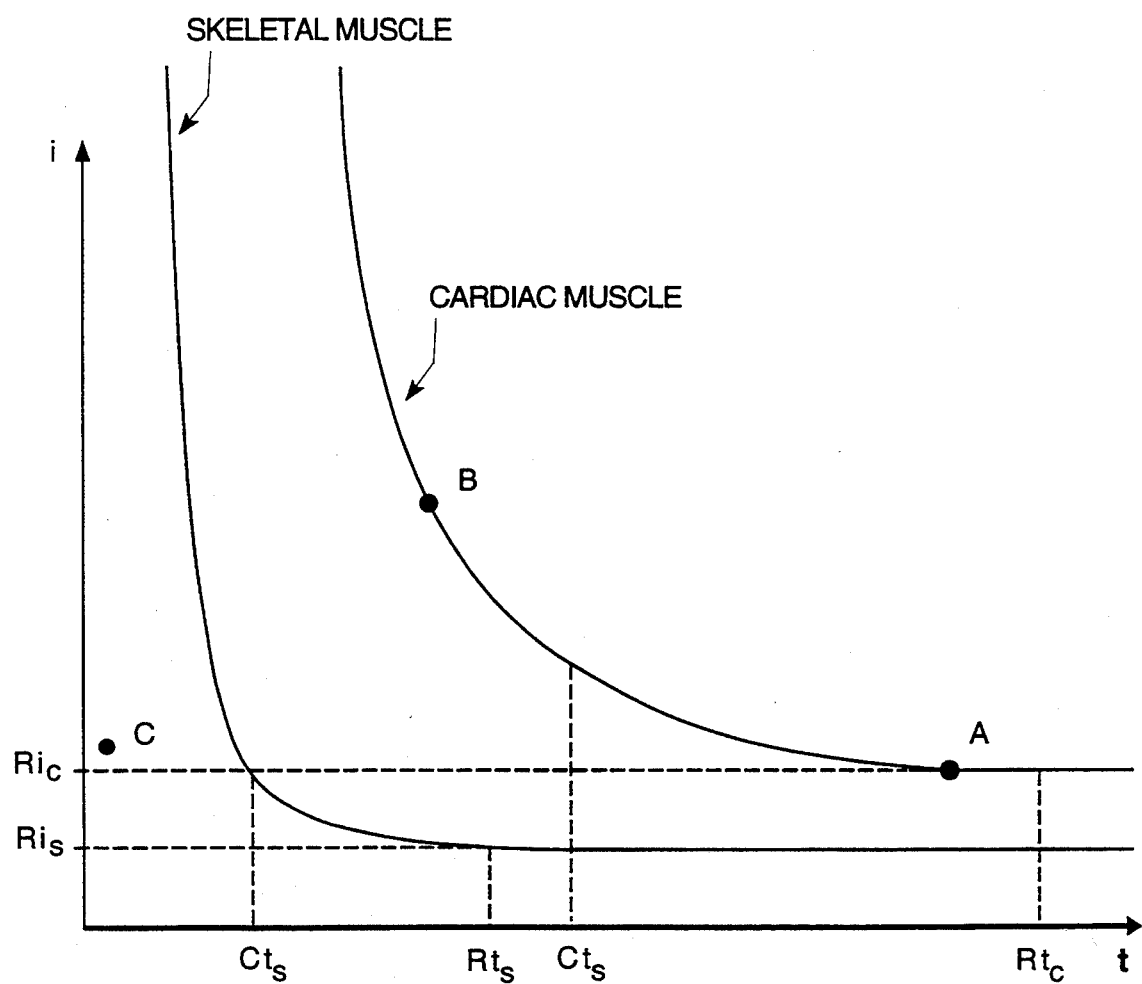
FIG. 6 shows plotted characteristics, one for cardiac muscle and one for skeletal muscle, relating a stimulating pulse's strength with the pulse's duration.

The pulse width $W_p$ and pulse period $T_p$ of each of the pulses in the pacing pulse trains are also selected based on a comparison of the strength-duration relationships for cardiac muscle and skeletal muscle (FIG. 6). As shown in FIG. 6, a minimum pulse duration, called the chronaxie ($Ct_c$ for cardiac muscle and $Ct_s$ for skeletal muscle), is the pulse duration corresponding to a stimulating pulse amplitude equal to twice the rheobase of a muscle. With a pulse stimulus having a duration shorter than the chronaxie, it becomes increasingly difficult to stimulate a corresponding muscle.

Considering the strength-duration curves of FIG. 6, the cardiac muscle's chronaxie $Ct_c$ is approximately equal to 2 msec and the skeletal muscle's chronaxie $Ct_s$ is approximately equal to 0.5 msec. A pulse stimulus of a duration shorter than the skeletal muscle chronaxie $Ct_s$, having, e.g., the duration of a pulse at point C, would therefore tend not to stimulate either cardiac muscle or skeletal muscle. However, a train of such pulses having suitably adjusted amplitudes and a pulse train duration $T_t$ which is longer than the cardiac muscle chronaxie $Ct_c$, e.g., the stimulus duration of point A, effectively stimulates the heart as if the pulse trains had been filtered by, e.g., the skeletal muscles, to produce a continuous pacing pulse.

Referring again to FIGS. 4A–4C, based on this consideration, the pulse width $W_p$ of each of the pacing pulses is selected to be less, preferably much less, than the skeletal muscle chronaxie $Ct_s$ (0.5 msec). With pulses of such width, the skeletal muscles tend to be stimulated less than they would if the pacing pulse were a single continuous pulse, but the heart is stimulated as effectively as a continuous pulse. The pacing pulse width $W_p$ for achieving this condition is preferably less than 100 microseconds, and most preferably less than 15 microseconds. Pulse widths of less than about 7 microseconds may produce a pacing pulse frequency which is high enough to cause tissue damage, and thus may need to be avoided. Given the selected pulse width $W_p$, the pacing pulse period $T_p$ is selected to ensure adequate pacing stimulation, or capture, of the heart.

The preferred pacing pulse duty cycle ($W_p$ divided by $T_p$) is 50%, but a lower duty cycle (e.g., 20%), a higher duty cycle (e.g., 66% so that the waveforms overlap), or a variable duty cycle may be used, provided the given duty cycle is adequate to capture the heart. Generally speaking, the higher the duty cycle, the higher will be the effective filtered amplitude of the continuous pulse that influences the cardiac muscle.

The duty cycle of pacing stimuli 80 equals the lesser of the sum of the pacing pulse duty cycles of waveforms 82, 84 or 100%. For example, if the pacing pulse duty cycle of waveforms 82, 84 are each 50%, the duty cycle of pacing stimuli 80 is 100%. Similarly, the duty cycle of pacing stimuli 80 is 100% when the pacing pulse duty cycles of waveforms 82, 84 are each 75% and the duty cycle of pacing stimuli 80 is 90% when the pacing pulse duty cycle of waveform 82 is 60% and the pacing pulse duty cycle of waveform 84 is 30%.

Figure 7A:
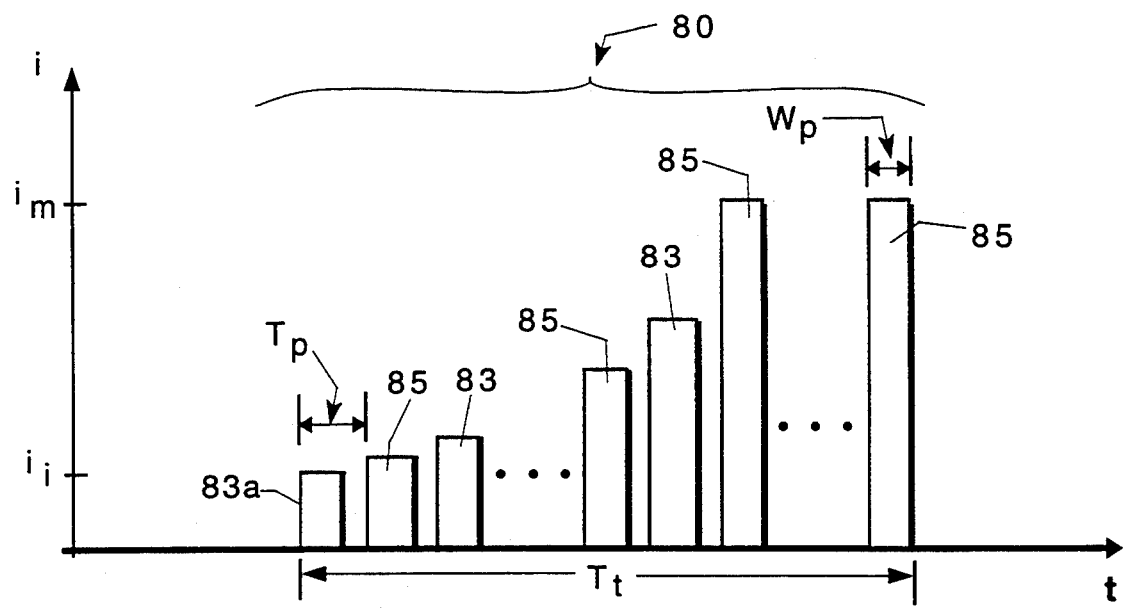
FIGS. 7A and 7B are illustrative examples of alternative electrical pacing stimuli produced by the signal generator of FIG. 1.

A variation in the form of a pacing stimulus 80 is shown in FIG. 7A. The amplitude, $i_s$, of the first pulse 83a in each pacing pulse train has a subthreshold amplitude, i.e., the amplitude is below the minimum pulse amplitude required for skeletal muscle stimulation if the pulse amplitude of a given pacing pulse train remained constant for the duration of the pulse train. Each of the pulses 83, 85 following the initial pulse has an amplitude greater than that of the previous pulses, with some number of trailing pulses 83, 85 all having a maximum current amplitude, $i_M$. The value of this maximum current amplitude $i_M$ is selected, along with other pulse train characteristics, e.g., pulse train duration, to ensure capture of the heart. For example, a pulse train with a given number of pulses having a maximum current amplitude $i_M$ may require a shorter duration to capture the heart than a pulse train with fewer pulses having a maximum current amplitude that is greater than $i_M$. Pacing stimulus 80 is then time multiplexed using, for example, the technique illustrated in FIG. 4 to produce a waveform that includes pulses 83 and flows along path 74, and a waveform that includes pulses 85 and flows along path 76.

The use of initial, subthreshold pulses, followed by a series of pulses each having an amplitude that is greater than the amplitudes of the preceding pulses is intended to induce accommodation of the skeletal muscles to the pacing pulse train stimuli. Accommodation of a muscle is a physiological phenomenon which can be induced by gradually, rather than abruptly, exposing a muscle to a stimulus amplitude, whereby the stimulating threshold of the muscle is increased beyond the magnitude of the applied stimulus. An accommodated muscle or nerve requires a higher than normal stimulus magnitude to be effectively stimulated, and may even reject stimulation altogether for any magnitude of stimulus increase.

Figure 7B:
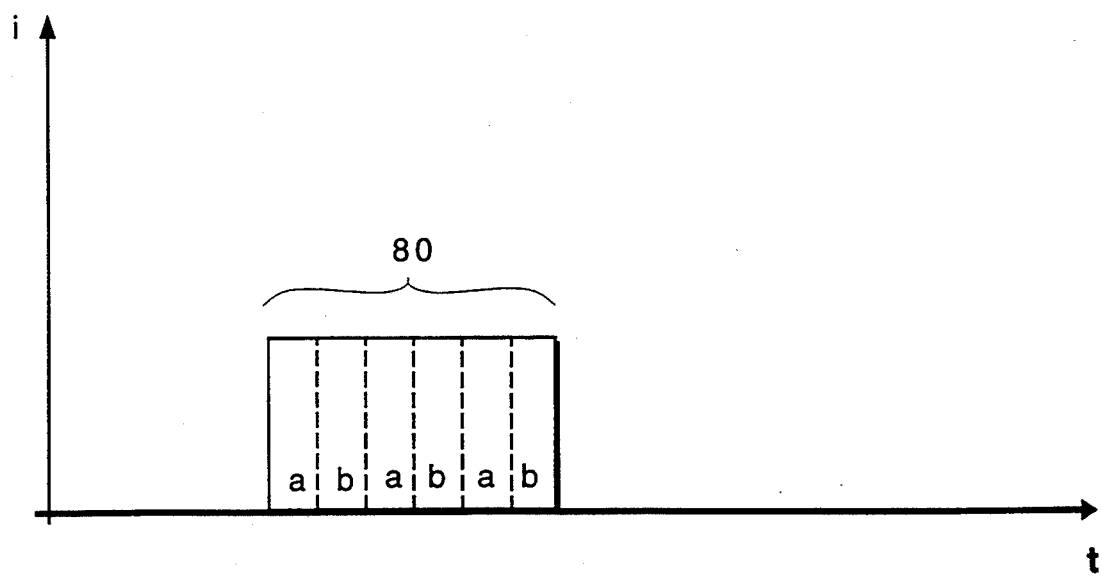

FIG. 7B illustrates another variation in the form of a pacing stimulus 80 in which pacing stimulus 80 is a continuous pulse including alternating portions 80a and 80b. Pacing stimulus 80 is then time multiplexed using the technique illustrated in FIG. 5 to produce a waveform that includes portions 80a and flows along path 74, and a waveform that includes pulses 80b and flows along path 76.

Given the physiological differences between cardiac muscle and skeletal muscle, the amplitudes of the pulses in the pacing pulse train are selected to cause accommodation of skeletal muscles but not to cause accommodation of cardiac muscle. By simultaneously achieving these conditions, the pacing pulse trains effectively stimulate the heart but tend to decrease the skeletal muscle stimulation typically associated with the transcutaneous cardiac muscle stimulation.

While effectively stimulating the heart with decreased skeletal muscle stimulation, the pacing pulse trains also appear to decrease the cutaneous nerve stimulation associated with transcutaneous cardiac pacing. Because the skeletal muscles and cutaneous nerves have similar chronaxies (FIG. 6), the cutaneous nerves, like skeletal muscles, tend to be stimulated less by the pulses in the pacing pulse trains than they would if the pacing pulse were a single continuous pulse.

Referring again to FIG. 1, the signal generator's waveform-shaping circuitry 60 modifies the stream of pulses generated by the oscillator circuitry 40 to create the pacing pulses in the pacing stimuli 65. The timing and control circuitry 20 provides further fine adjustment of the pacing pulse characteristics, for example, pulse shape. Both the waveform-shaping circuitry 60 and the timing and control circuitry 20 may be programmed to include or omit any or more of the electrical signal characteristics discussed above.

Figure 8:
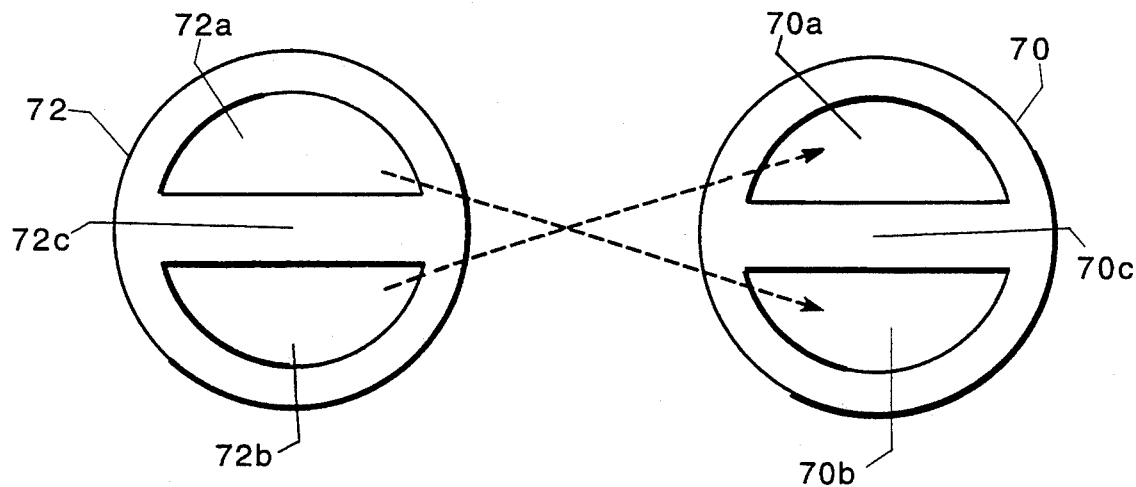
FIGS. 8 and 9 are schematics of electrode configurations according to the invention.

Another suitable electrode configuration is shown in FIG. 8, where the electrodes 70, 72 are divided into top regions 70a, 72a and bottom regions 70b, 72b. In operation, waveform 82 flows from top region 72a to bottom region 70b and waveform 84 flow from top region 72b to bottom region 70a. Top regions 70a, 72a, are separated from their corresponding bottom regions 70b, 72b, by middle regions 70c, 72c, the widths of which are adequate to provide electrical isolation between the top and bottom regions. The width of middle regions 70c, 72c can vary from about 0.001 inches to 2 inches. Improved distribution of current density has been achieved when the widths of middle regions 70c, 72c are about one half inch. The middle regions 70c, 72c may be filled with an adhesive to act as an insulating material between the top 70a, 72a and bottom 70b, 72b electrode regions.

Figure 9:
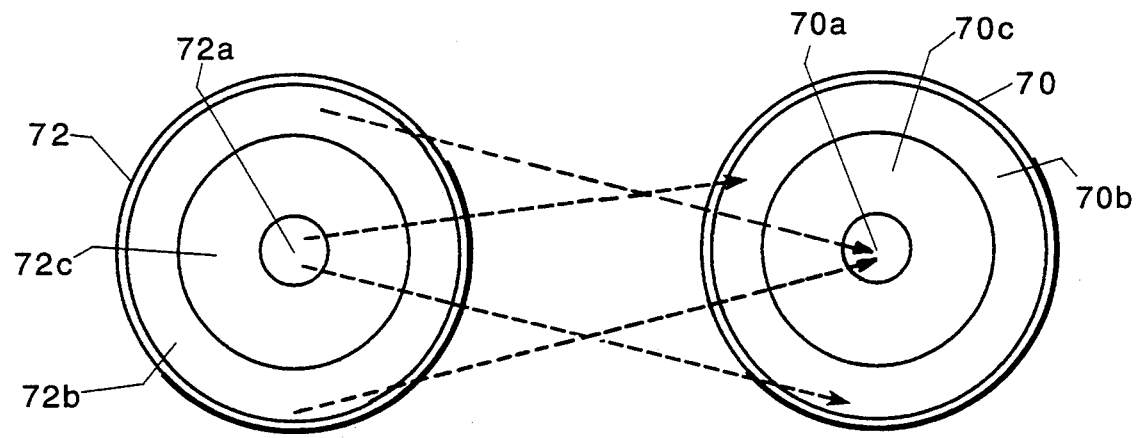

Yet another suitable electrode configuration is shown in FIG. 9, where the electrodes 70, 72 are divided into central, isolated regions 70a, 72a and surrounding annular regions 70b, 72b. In operation, waveform 82 flows from central region 72a to surrounding region 70b and waveform 84 flow from surrounding region 72b to central region 70a. Central regions 70a, 72a, are separated from their corresponding surrounding regions 70b, 72b, by lateral regions 70c, 72c, the widths of which are similar to those discussed with respect to FIG. 8.

A variety of other electrode structures may be used to deliver the pacing stimuli. In view of the reduced skeletal muscle and cutaneous nerve stimulation that is achieved by the pacing stimuli, the contribution of the electrode configuration to stimulation reduction may be less important. Thus, conventional noninvasive pacing electrodes with nonmetallic skin-contacting members, such as those disclosed in U.S. Pat. No. 4,349,030, or as sold by R-2, of Morton Grove, Ill., Physio-Control Corporation, of Redmond, Wash., or ZMI Corporation, of Woburn, Mass., are suitable for delivering the pacing pulse trains. Alternatively, electrodes having metallic skin-contacting members may be adapted to deliver the pacing stimuli.

Figure 10A:
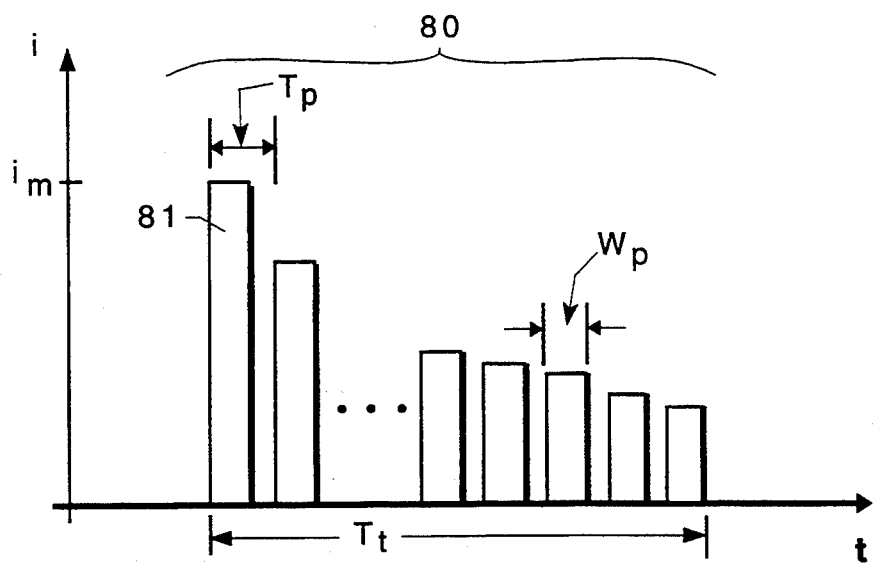
FIGS. 10A–10C are three illustrative examples of alternative pacing stimuli produced by the signal generator of FIG. 1.
Figure 10B:
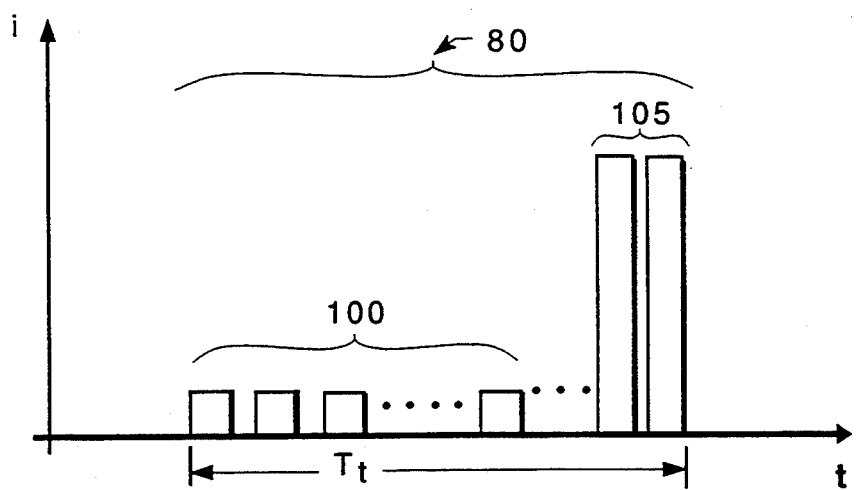
Figure 10C:
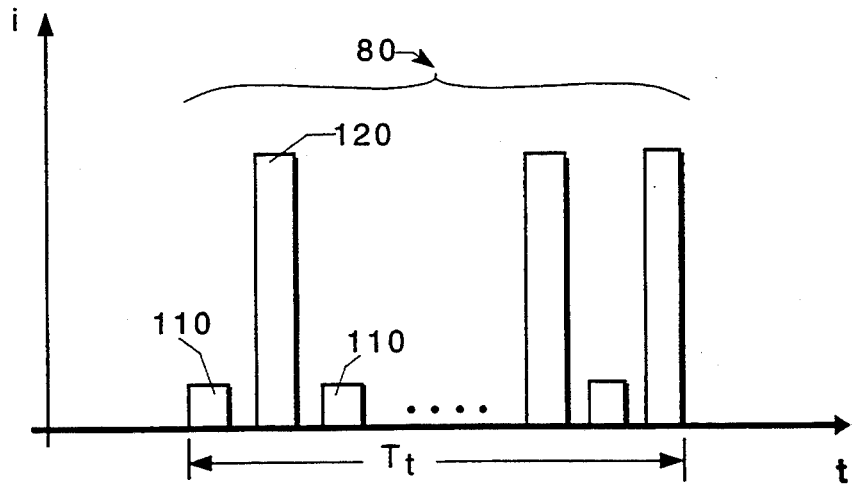

Other embodiments of the invention are within the claims. For example, referring to FIG. 10A, pacing stimulus 80 could include a pulse train having an initial pulse 81 with a maximum amplitude $i_m$, followed by a series of pulses 83, 85 which each have an amplitude that is less than the amplitudes of all preceding pulses. As shown in FIG. 10B, pacing stimulus 80 could include a pacing pulse train having an initial portion 100 of subthreshold pulses 83, 85, all of an equal amplitude, followed by a portion 105 of above-threshold pulses, all of an equal amplitude. The initial portion 100 of subthreshold pulses may include a second portion of subthreshold pulses, all of a second, equal amplitude. Alternatively, as shown in FIG. 10C, the pacing pulse train could have alternating subthreshold pulses 110 and above threshold pulses 120. Another variation for achieving the subthreshold pulses is to vary the duration of the pulses, using shorter durations for the subthreshold pulses, and longer durations for the above-threshold pulses. Pacing stimuli 80 of each of FIGS. 10A–10C are time multiplexed using techniques such as those illustrated in FIGS. 4A–4C, 5A–5C, 12A–12C, and 13A–13C to produce waveforms that flow along path 74, and waveforms that flow along path 76.

Given any pulse combination in a pacing pulse train, the pulses in a train could have non-rectangular shapes, e.g., triangular, exponential, or rounded. The duty cycle and duration of pulses can be varied within the pulse train (e.g., there could be brief gaps in the sequence of pulses). Background stimulation (e.g., a train of subthreshold pulses) could be superimposed continuously or just in the intervals between pacing stimuli to further reduce discomfort (as disclosed in U.S. Pat. No. 5,205,284 entitled Method and Apparatus for Transcutaneous Electrical Cardiac Pacing with Background Stimulation, hereby incorporated by reference).

Figure 11:
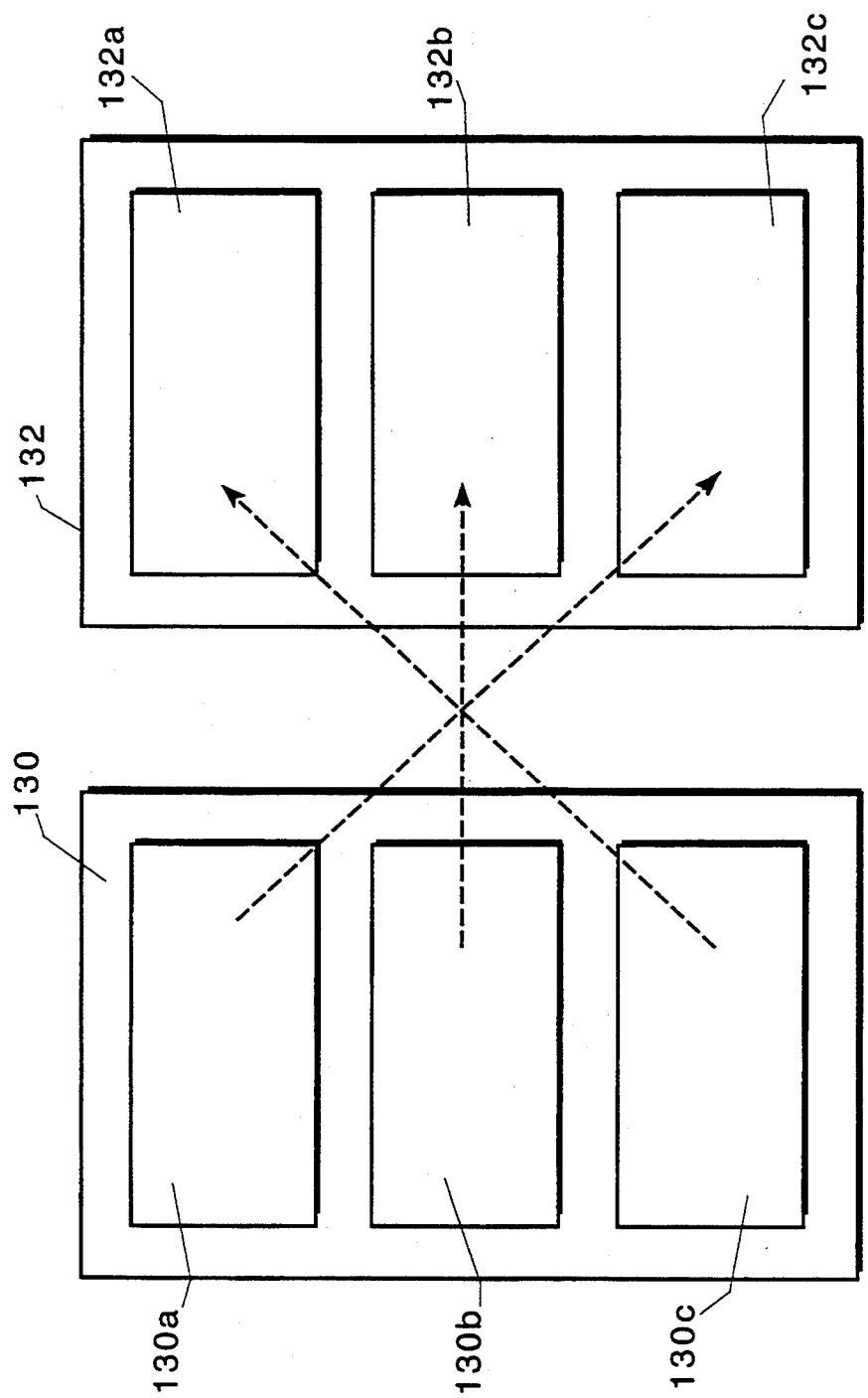
FIG. 11 is a schematic of an electrode configuration according to the invention.

Each electrode in a pair of electrodes could be divided into more than two regions. For example, as shown in FIG. 11, each electrode 130, 132 could include three rectangular regions 130a–130c, 132a–132c arranged adjacent to each other. In this case, electrodes 130, 132 would be connected to signal generator 10 so that current flows between regions 130a and 132c, regions 130b and 132b, and regions 130c and 132a.

What is claimed is:

1. Apparatus for transcutaneously pacing a heart at a pacing rate, the apparatus comprising
   stimuli generating circuitry configured to generate electrical stimuli that include pacing stimuli delivered at an output at the pacing rate,
   electrodes connected to the output of the stimuli generating circuitry and configured to deliver the electrical stimuli to a patient, said electrodes including a plurality of electrode pairs, wherein each said pacing stimulus comprises a plurality of series of individual pulses,
   wherein at least one of said series of individual pulses is delivered by an electrode pair that differs from an electrode pair that delivers another of said series of individual pulses.

2. The apparatus of claim 1 wherein the individual pulses of said pacing stimuli have durations and amplitudes making said pacing stimuli capable of causing a contraction of the heart, but each series of individual pulses incapable, by itself, of causing such a contraction.

3. The apparatus of claim 1 wherein said individual pulses making up said pacing stimuli, when combined together, form a substantially continuous pulse.

4. The apparatus of claim 1 wherein said individual pulses making up said pacing stimuli, when combined together, remain a series of individual pulses.

5. The apparatus of claim 4 wherein the amplitude of said pacing stimulus in the interval between individual pulses in said single series of individual pulses is less than the threshold amplitude for stimulating cardiac muscle for a continuous pulse of the same duration.

6. The apparatus of claim 1 wherein each pacing stimulus comprises a first series of individual pulses and a second series of individual pulses, said first series of individual pulses being transmitted between a first electrode pair comprising a first electrode and a second electrode, and said second series of individual pulses being transmitted between a second electrode pair comprising a third electrode and a fourth electrode.

7. The apparatus of claim 6 wherein said first, second, third, and fourth electrodes are arranged so that an electrical path between said first and second electrodes intersects an electrical path between said third and fourth electrodes.

8. The apparatus of claim 7 wherein said electrical paths intersect at the heart.

9. The apparatus of claim 6 wherein said first and third electrodes are mounted on the same substrate so that both electrodes may be applied simultaneously to the patient's chest, and said first electrode is spaced laterally from said third electrode.

10. The apparatus of claim 9 wherein the lateral spacing between said first and third electrodes is between about 0.001 and 2 inches.

11. The apparatus of claim 10 wherein the lateral spacing between said first and third electrodes is between 0.25 and 0.75 inches.

12. The apparatus of claim 11 wherein the lateral spacing between said first and third electrodes is between 0.475 and 0.525 inches.

13. The apparatus of claim 9 wherein said first electrode laterally surrounds said third electrode.

14. The apparatus of claim 13 wherein said fourth electrode is spaced laterally from said second electrode and laterally surrounds said second electrode.

15. The apparatus of claim 9 wherein said first electrode is circular and said third electrode is annular.

16. The apparatus of claim 1, 2, 5, or 9 wherein each individual pulse has a duration and amplitude making it incapable, by itself, of causing a contraction of the heart.

17. The apparatus of claim 1 wherein no pulse in any of said series of individual pulses overlaps a pulse in another of said series of individual pulses by more than 50%.

18. The apparatus of claim 17 wherein no pulse in any of said series of individual pulses overlaps a pulse in another of said series of individual pulses by more than 25%.

19. The apparatus of claim 18 wherein no pulse in any of said series of individual pulses overlaps a pulse in another of said series of individual pulses by more than 5%.

20. The apparatus of claim 17 wherein no pulse in any of said series of individual pulses overlaps a pulse in another of said series of individual pulses.

21. The apparatus of claim 1 wherein said plurality of electrode pairs comprises more than two electrode pairs.

22. A method of transcutaneously pacing a heart at a pacing rate, the method comprising the steps of:
generating electrical stimuli including pacing stimuli delivered at a pacing rate, the pacing stimuli comprising a plurality of series of individual pulses;
delivering a first series of individual pulses to a patient through a first pair of electrodes; and
delivering a second series of individual pulses to a patient through a second pair of electrodes.

23. The method of claim 22 wherein the individual pulses of said pacing stimuli have durations and amplitudes making said pacing stimuli capable of causing a contraction of the heart, but each series of individual pulses incapable, by itself, of causing such a contraction.

24. The method of claim 22 wherein said individual pulses making up said pacing stimuli, when combined together, form a substantially continuous pulse.

25. The method of claim 22 wherein said individual pulses making up said pacing stimuli, when combined together, remain a series of individual pulses.

26. The method of claim 25 wherein the amplitude of said pacing stimulus in the interval between individual pulses in said single series of individual pulses is less than the threshold amplitude for stimulating cardiac muscle for a continuous pulse of the same duration.

27. The method of claim 22, said method further including the step of arranging said first and second pairs of electrodes so that an electrical path between electrodes in said first pair of electrodes intersects an electrical path between electrodes in said second pair of electrodes.

28. The method of claim 27 wherein said arranging step further includes arranging said electrodes so that said electrical paths intersect at the heart.

29. The method of claim 22 wherein no pulse in any of said series of individual pulses overlaps a pulse in another of said series of individual pulses by more than 50%.

30. The method of claim 29 wherein no pulse in any of said series of individual pulses overlaps a pulse in another of said series of individual pulses by more than 25%.

31. The method of claim 30 wherein no pulse in any of said series of individual pulses overlaps a pulse in another of said series of individual pulses by more than 5%.

32. The method of claim 31 wherein no pulse in any of said series of individual pulses overlaps a pulse in another of said series of individual pulses.

33. The method of claim 22, 23, 26, or 29 wherein each individual pulse has a duration and amplitude making it incapable, by itself, of causing a contraction of the heart.

34. The method of claim 22, said method further including delivering a third series of individual pulses to a patient through a third pair of electrodes.

* * * * *

UNITED STATES PATENT AND TRADEMARK OFFICE
CERTIFICATE OF CORRECTION

PATENT NO.   : 5,431,688

DATED        : July 11, 1995

INVENTOR(S)  : Gary A. Freeman

It is certified that error appears in the above-identified patent and that said Letters Patent is hereby corrected as shown below:

```
    Col. 3, line 39, "figure" should be --figures--.

Col. 3, line 43, "(FIG. 5A)" should be --(FIG. 5B)--.

Col. 3, line 44, "(FIG. 5A)" should be --(FIG. 5C)--.

Col. 3, line 51, "(FIG. 5B)" should be --(FIG. 12A)--.

Col. 3, line 60, "figure" should be --figures,--.

Col. 3, line 62, "(FIG. 13C)" should be --(FIG. 13B)--.

Col. 3, line 64, "(FIG. 5C(c))" should be
--(FIG. 13C)--.
```

Signed and Sealed this

Tenth Day of October, 1995

*Attest:*

BRUCE LEHMAN

*Attesting Officer*   *Commissioner of Patents and Trademarks*